United States Patent [19]
Nurse et al.

[11] Patent Number: 5,254,315
[45] Date of Patent: Oct. 19, 1993

[54] CARRIER DEVICE

[75] Inventors: Colin A. Nurse, Newark, Del.; Robert E. Bernstine, Chesapeake City, Md.

[73] Assignee: E. I. Du Pont de Nemours and Company, Wilmington, Del.

[21] Appl. No.: 736,155

[22] Filed: Jul. 26, 1991

[51] Int. Cl.$^5$ .............................................. B01L 9/06
[52] U.S. Cl. ..................................... 422/104; 422/99; 422/102; 422/61; 436/808
[58] Field of Search ............ 422/58, 61, 68.1, 99-100, 422/101-104; 436/808

[56] References Cited

U.S. PATENT DOCUMENTS

| Re. 29,725 | 8/1978 | Johnson et al. | 23/230 |
| 3,882,619 | 5/1975 | Durand et al. | 40/310 |
| 4,119,407 | 10/1978 | Goldstein et al. | 422/58 |
| 4,198,484 | 4/1980 | Reichler et al. | 435/296 |
| 4,397,725 | 8/1983 | Enzer et al. | 204/206 |
| 4,647,541 | 3/1987 | Guadagno et al. | 436/66 |
| 4,791,060 | 12/1988 | Chandler | 435/296 |
| 4,806,316 | 2/1989 | Johnson et al. | 422/100 |
| 4,865,813 | 9/1989 | Leon | 422/101 |
| 4,970,053 | 12/1990 | Fechtner | 422/102 |
| 5,000,923 | 3/1991 | Coville et al. | 422/102 |

Primary Examiner—Lyle A. Alexander

[57] ABSTRACT

An analytical carrier device permits the holding of a sample, reaction vessel with reagents for the sample, and a container for receiving a processed sample. The container facilitates transfer to an analytical device for analysis.

3 Claims, 2 Drawing Sheets

CARRIER DEVICE

CROSS REFERENCE TO RELATED PATENT APPLICATIONS

This invention discloses materials which is disclosed and/or claimed in a patent application entitled Vortex Mixer Drive, Ser. No. 07/736,177, filed Jul. 26, 1991 and also an application entitled Multilinear Automatic Apparatus for Processing Immunoassays, Ser. No. 07/736,157, filed Jul. 26, 1991.

FIELD OF THE INVENTION

This invention relates to a carrier device for holding samples which are to be analyzed in a manner which facilitates their combination with analysis reagents and apparatus for transferring the results for determination by further instrumentation.

BACKGROUND OF THE INVENTION

In the analytical field it is often necessary to process samples of reagents for analysis by combining them with various reagents, support particles and the like. Following such analysis, it is then necessary to transfer the processed sample held in a reaction device back to a device which facilitates processing the results. This is particularly true when the interim processing of a sample involves repeated steps that typically required immunoassay techniques. These include reaction time and wash cycles all involving the use or other particles to facilitate the chemical reactions. In a case of immunoassays, it is necessary to vortex the contents of a reaction vessel to maintain the particles suspended so that the reaction may go to completion. Such analysis may also present difficulties inasmuch as the samples may come from different units and all require mounting on the processing carrier. A further problem arises due to the combination of the samples and reagents during the processing. It is difficult to keep track of the proper sample to make sure it receives the processing needed and does not become mixed up with other samples so that the integrity of the analysis is lost.

SUMMARY OF THE INVENTION

Many of these problems are solved by the device of this invention which facilitates the analysis of samples in a reaction vessel. The device comprises a top member having an end portion, a support for the top member, a transparent container having analysis reagents contained therein and having a header containing an instruction code formed on the header, a sample cup being removably mounted on the top member adjacent the header, and a reaction vessel holder mounted by the top member in the end portion, whereby the sample may be positioned in the reaction vessel for reaction and thereafter transferred to the transparent container for analysis.

In a particularly preferred embodiment, the device of the invention is mounted to permit the sample to be nutated. The reaction vessel itself comprises an inner container having a longitudinal axis and which contains a first reagent and an outer container coaxially positioned about the upper portion of the inner container, the outer container having a second reagent. It is desirable that the transparent container be slidably removeable from the top member to facilitate its use and transfer for further analysis.

The apparatus of this invention maintains three units together, i.e., the sample, the reagent for analysis and the ultimate processed sample in a separate container. This facilitates processing samples and maintains all the units necessary for analysis together during the analysis time interval. Multiple sample cups may be simply clipped on to the carrier for use with different sample input and separate incubation is permitted by the structure of the carrier for material within the reaction vessel.

BRIEF DESCRIPTION OF THE DRAWINGS

This invention will be more clearly understood when considered in conjunction with the accompanying drawings in which like reference numerals refer to like components in each of the drawings, in which.

DETAILED DESCRIPTION OF THE PREFERRED EMBODIMENT

Figure 1:
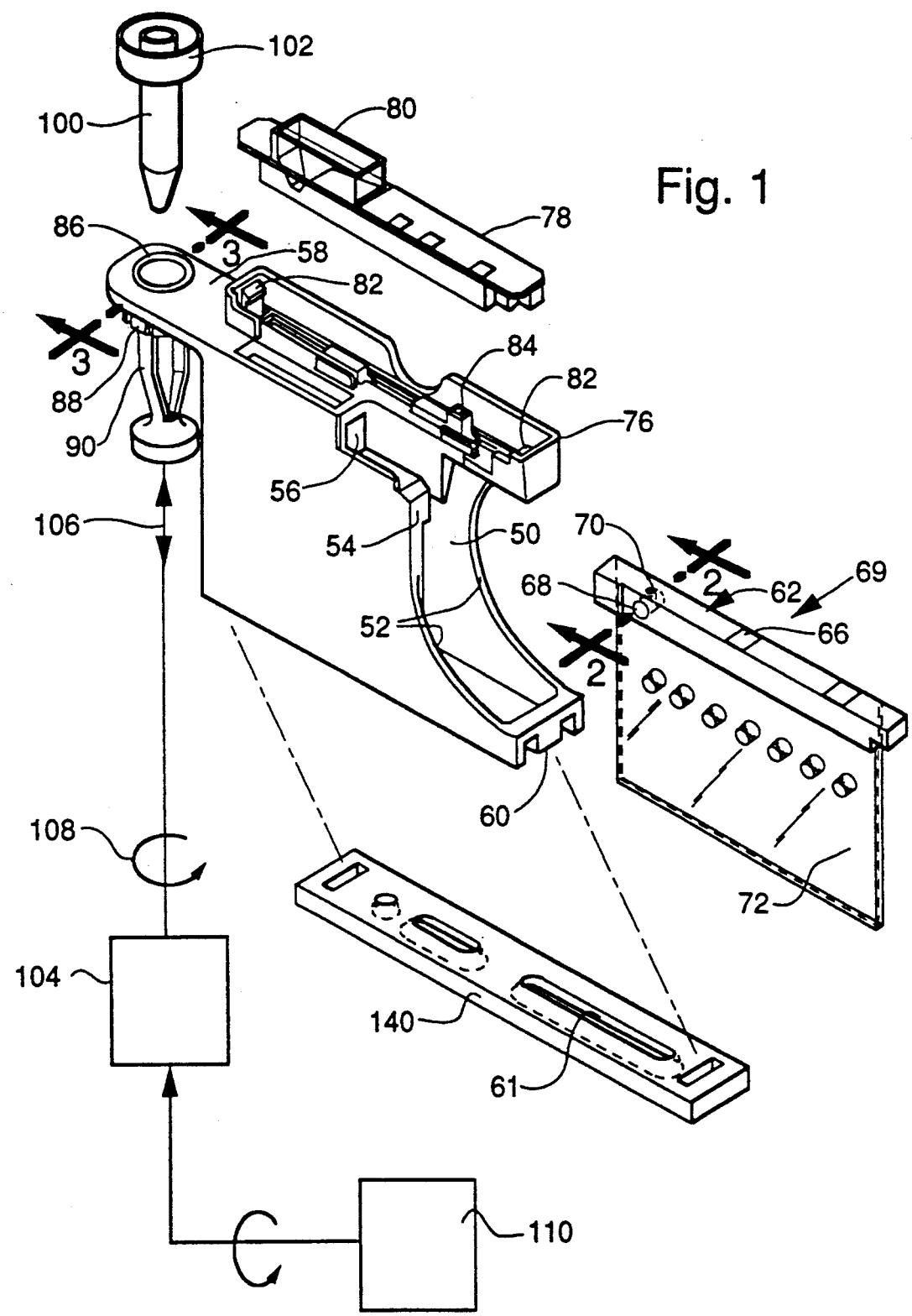
FIG. 1 is an exploded view of the carrier device constructed in accordance with this invention.
Figure 2:
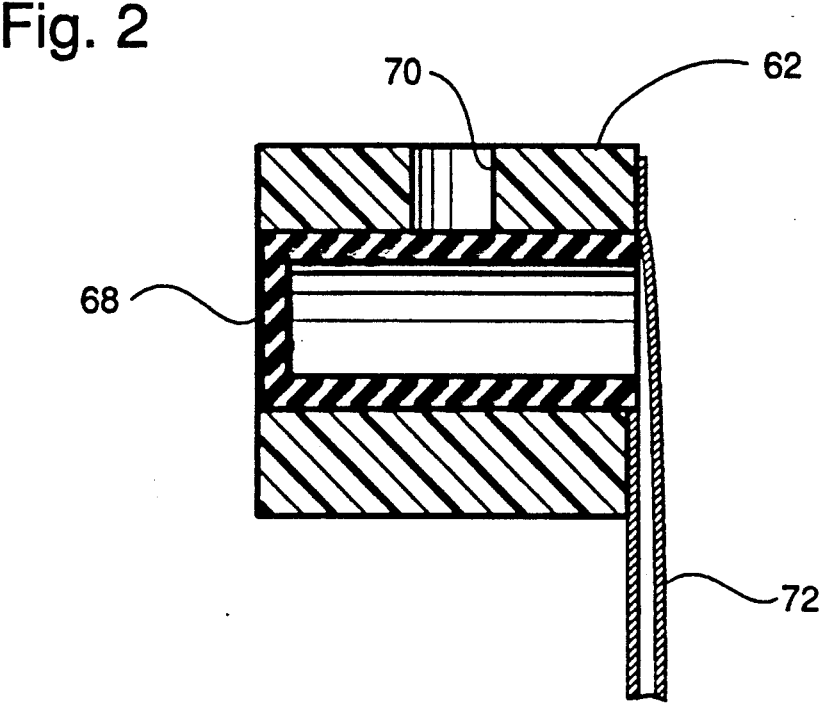
FIG. 2 is a section taken through the stopper of a container along the lines 2—2 of FIG. 1.
Figure 3:
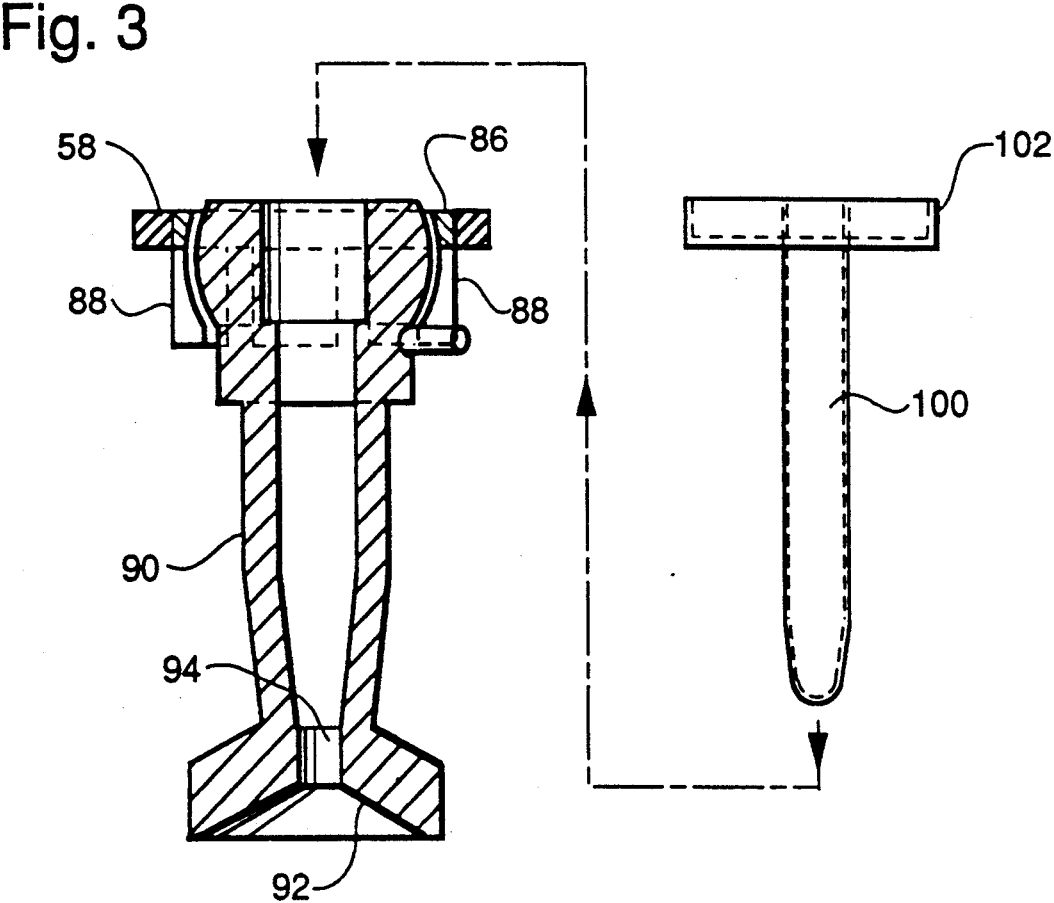
FIG. 3 is a section taken along the lines 3—3 of FIG. 1 particularly depicting the construction of the reaction vessel holder.

There may be seen in FIGS. 1, 2, and 3, exploded sectional views of one of the carriers constructed in accordance with this invention. The carrier is seen to contain a hollow, molded housing 50 defined by a pair of sidewalls 52, a top plate 58, and a base support 60. A drive bar 140 is positioned in the lower portion between the sidewalls and secured to the base support as by glueing. This bar 140 has receptacles 61 to facilitate its receiving driving or positioning pins for positioning the bar 140 and hence the carrier. The housing 50 may be formed of polysulfone or any other suitable engineering plastic which is rigid, strong and chemically inert. Attached to the front sidewall (in the drawing) is a partition 54 which cooperates with the top 58 to accommodate the header top frame 62 of an analytical container or pack 69 which may be the same and preferably is the same as the analytical pack used in the aca ® Automatic Clinical Analyzer sold by E. I. du Pont de Nemours and Company, Wilmington, Del., U.S.A. The analytical pack has identifying indicia 66 on the top, which may be read by appropriate sensors to indicate the particular test being run, and includes transparent plastic pack 72 supported by the header 62 and a hollow septum 68 with an orifice 70 which may be used to introduce materials into the pack 72. Since the analytical container 62 is well known it will not be described further.

In any event, the partition 54 and top 58 cooperate to define an orifice 56 adapted to accommodate the top member 62 of the analytical pack 69 so it may be inserted into the carrier which is formed of plastic material. The side pack is to slide in between the two walls 52. The top of the carrier 50 also includes an elongated cup-like member 76 which is adapted to receive a removable sample cup 78 containing a container 80. The sample cup 78 is held in the position within the opening 76 by appropriate molded grips 82. A fitting feature 84 may be provided for the sample cup 78 to control access to the opening.

To complete the carrier, the end of the top member 58 may have an orifice 86 with downwardly extending flanges 88 adapted to hold a reaction vessel holder 90. The flanges 88 are concave on the inside to define a socket which cooperates with the bulbous top on a reaction vessel holder 90 in a ball and socket joint manner. The lower portion of the reaction vessel holder 90 may be shaped as to have an inverted cavity or receptacle 92 at the upper end of which is a bore 94 adapted to receive a pin from a nutating drive member.

In an alternative embodiment of this invention, the reaction vessel 100 holder 90 may be the reaction vessel itself although the use of the holder is preferred for its long term stability and reliability. If the reaction vessel holder 90 is adapted to separate reaction vessel 100, the vessel 100 has at the upper portion thereof a concentric chamber 102 for holding reaction reagents that typically may be used, for example, in an immunoassay process.

The reaction vessel holder 90 is nutated by an automatic apparatus 104. Although any suitable drive apparatus may be used that provides two directions of linear motion and one direction of rotary motion, that described in copending application Ser. No. 07/736,157, filed on Jul. 26, 1991, is one that has been used successfully. This drive apparatus provides a bidirectional motion as depicted by the line 106 (FIG. 1) as well as rotational motion as depicted by the line 108 to the reaction vessel holder 90. The drive apparatus is powered by a single bidirectional drive motor 110 which provides rotational motion to the automatic apparatus 104. The automatic apparatus engages the reaction vessel holder 90 by elevating a mixing cylinder (not shown) on which a pin is positioned contiguous the periphery at a point off the elongated axis of the mixing cylinder. In other words the pin engages the bottom end of the reaction vessel holder 90 in a position which is eccentric to the axis which mounts the mixing cylinder. The apparatus then spins the cylinder moving the engaged end of the vessel holder 90 into an orbit. If the vessel holder 90 is mounted so that it is free in two rotational directions of freedom, then the contents of the reaction vessel holder 90 will swirl or nutate thus mixing them. Reversal of the drive 110 which spins the reaction vessel holder 90 stops the orbiting of the vessel 100 and lowers the cylinder thus disengaging the cylinder from the reaction vessel holder 90.

The carrier device just described has many advantages and it permits in effect the combination of three different functions into a single device. Firstly, sample cups from various analysis devices holding the sample may be snapped into place in the upper portion of the device. Secondly, a reaction vessel 100 containing reagents for the analysis of samples may be inserted into a reaction vessel holder 90 which may be inserted into and processed separately from the carrier. Thirdly, the completed reacted sample with reagents may be introduced into the analytical pack 62 which is slidably removeable from the carrier for subsequent processing and analysis is desired in other machines.

We claim:

1. An analytical carrier device for processing samples held in a reaction container comprising:
   a hollow vessel comprising a top side and other sides defining a hollow chamber within the vessel wherein the top side has an exterior top side that is not within the hollow chamber,
   a support member having an identifying indicia and a transparent container attached to the support member wherein the support member is constructed and adapted to be slidable within the chamber of the vessel,
   a sample container constructed and adapted to be removably mounted to the exterior top side of the vessel,
   a reaction container holder constructed and adapted to hold the reaction container and to be mounted on the exterior top side wherein the reaction container holder is further constructed and adapted to be agitated independently from the hollow vessel to facilitate the mixing of the contents in the reaction container.

2. An analytical carrier device as set forth in claim 1 wherein the reaction vessel holder includes a reaction vessel positioned in the holder.

3. An analytical carrier device as set forth in claim 2 wherein the reaction vessel comprises an inner container having a longitudinal axis and which contains a first reagent and an outer container coaxially positioned about the upper portion of the inner container, the outer container having a second reagent.

* * * * *